United States Patent [19]

Milner

[11] 4,340,764

[45] Jul. 20, 1982

[54] PROCESS FOR THE PREPARATION OF 1,4-DIALKYLBUT-2-ENE-1,4-DIONES

[75] Inventor: David J. Milner, Whitefield, England

[73] Assignee: Imperial Chemical Industries Limited, London, England

[21] Appl. No.: 207,613

[22] Filed: Nov. 17, 1980

[30] Foreign Application Priority Data

Jan. 11, 1980 [GB] United Kingdom ................ 8001011

[51] Int. Cl.$^3$ ............................................ C07C 45/57
[52] U.S. Cl. .................................................. 568/386
[58] Field of Search ........................................ 568/386

[56] References Cited

U.S. PATENT DOCUMENTS 3,931,270 1/1976 Evers et al. ......................... 568/386
3,981,920 9/1976 Buchi .................................. 568/386
4,082,717 4/1978 Brennan et al. ..................... 568/386

FOREIGN PATENT DOCUMENTS 1505667 3/1978 United Kingdom ................ 568/386

OTHER PUBLICATIONS

Held et al., Biochem & Biophys. Res. Comm., vol. 81, #3, pp. 878-885 (1978).
J.A.C.S., vol. 86, pp. 3879-3880, 1964, Foote et al.
Adam et al., J.A.C.S., vol. 102, pp. 404-406. (1980).
Koch et al., Chem. Ber., pp. 1984-1990 (1966).
Novilskii et al., Chem. Abst, vol. 59, #11394f (1963).
Brown et al., Can. J. Chem, vol. 35, p. 236, (1957).
Australian, J. of Chem., vol. 26, p. 2671 (1973).

Primary Examiner—Natalie Trousof
Assistant Examiner—James H. Reamer
Attorney, Agent, or Firm—Cushman, Darby & Cushman

[57] ABSTRACT 1,4-Dialkylbut-2-ene-1,4-diones are obtained by oxidizing a 2,5-dialkylfuran with an aqueous solution of an inorganic hypochlorite at a pH from 7 to 10.

7 Claims, No Drawings

PROCESS FOR THE PREPARATION OF 1,4-DIALKYLBUT-2-ENE-1,4-DIONES

This invention relates to an improved process for the preparation of 1,4-dialkylbut-2-ene-1,4-diones which are useful as intermediates in the synthesis of certain fungicides.

W. H. Brown and G. F. Wright, Canadian Journal of Chemistry, 35, 236 (1957), describe the preparation of trans-2,2,7,7-tetramethyloctane-3,6-dione by treating 2,5-di-tertbutylfuran with excess aqueous sodium hypochlorite solution followed by acidification of the mixture with hydrochloric acid. However the yield was only 25%, which is unacceptably low for an industrial process.

It is also known (Australian Journal of Chemistry, 26, 2671 (1973)) to use chromium trioxide in pyridine for this kind of oxidation. The yield of diketone, based on 2,5-di-tertbutylfuran actually consumed, is 70%, but this is an unattractive process on the industrial scale because of the large quantities of chromium trioxide that are required.

It has now been found that 1,4-dialkylbut-2-ene-1,4-diones can be obtained in high yields from 2,5-dialkylfurans by hypochlorite oxidation under carefully controlled conditions.

According to the present invention there is provided a process for the preparation of 1,4-dialkylbut-2-ene-1,4-diones which comprises oxidising a 2,5-dialkylfuran with an aqueous solution of an inorganic hypochlorite at a pH from 7 to 10, preferably pH 7.5 to 8.5.

The inorganic hypochlorite which is used as oxidising agent in the above-defined process may be, for example, calcium hypochlorite, potassium hypochlorite or preferably, because of its ready availability, sodium hypochlorite.

The process is preferably carried out at room temperature and in the presence of an inert organic solvent for the dialkylfuran. Suitable solvents are, for example, methylene chloride, chloroform, carbon tetrachloride and petroleum ether.

The invention also includes the 1,4-dialkylbut-2-ene-1,4-diones obtained according to the above process.

The 2,5-dialkylfuran starting materials for use in the process of the invention are preferably of the formula:

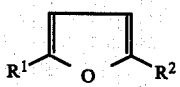
(I)

wherein $R^1$ and $R^2$ are each independently an alkyl radical containing from 1 to 4 carbon atoms. Oxidation of compounds of formula (I) above according to the process of the present invention gives diketones of the formula:

which are valuable intermediates for the synthesis of compounds having fungicidal and plant growth regulating properties such as are described in German Offenlegungsschrift No. 2819879. A particularly useful compound of formula (II) is that in which $R^1$ and $R^2$ are each tertbutyl, i.e. 2,2,7,7-tetramethyloct-4-ene-3,6-dione.

The process of the invention may be carried out by stirring together the dialkylfuran, inert organic solvent and aqueous hypochlorite solution and adjusting the pH of the aqueous phase to within the desired range by addition of a strong mineral acid such as hydrochloric acid. As reaction proceeds, the pH decreases slowly and is maintained within the desired range by addition of dilute aqueous alkali, for example, aqueous sodium hydroxide solution. Alternatively, the pH of the reaction mixture may be maintained within the desired range by buffering the aqueous hypochlorite solution. An example of a suitable buffer is borax (sodium tetraborate decahydrate). Other buffers may be used. Reaction is generally complete in two hours or less. The diketone reaction product is in the organic phase and can be recovered from the solution by conventional means. Yields of 90% are readily obtained.

The invention is illustrated by the following Examples in which percentages are by weight:

EXAMPLE 1

A mixture of 2,5-di-tertbutylfuran (0.916 g; 0.0051 mol) dodecane (0.2 g; glc internal standard) methylene chloride (20 ml), water (17.5 ml) and aqueous sodium hypochlorite solution in the form of industrial bleach (2.55 ml; equivalent to 0.0051 mol of sodium hypochlorite) were stirred together in a vessel fitted with a pH probe. The initial pH of the aqueous phase was 11.9, and this was reduced to 8.0 by the addition of 2 M hydrochloric acid (0.95 ml). The pH of the stirred aqueous phase was found to decrease slowly and was kept at 8.0 by dropwise addition of 1 M aqueous sodium hydroxide solution. Examination of the organic phase by gas-liquid chromatography showed that after 45 minutes about 90% of the initial 2,5-di-tertbutylfuran had been converted into 2,2,7,7-tetramethyloct-4-ene-3,6-dione.

EXAMPLE 2

Aqueous sodium hypochlorite solution (industrial bleach) was saturated with borax and the saturated solution (0.18 mol of sodium hypochlorite, about 150 ml) (Note 1) was charged to a 1 liter vessel. A solution of 2,5-di-tert. butylfuran (88% strength, 32.5 g, 0.16 mol) in methylene chloride (100 ml) was added to the buffered sodium hypochlorite solution and the mixture was stirred. With continuous agitation of the mixture at room temperature there was added gradually over a period of 40 minutes (Note 2) 2 N-hydrochloric acid in an amount sufficient to bring the pH of the aqueous phase to 8.5, the desired value, from an initial value of 10.2. 38 ml of 2 N hydrochloric acid were required (Note 3). The reaction mixture was stirred for 2 hours and the pH of the aqueous phase fell to 7.8. The upper organic layer (Note 4) was separated and found to contain 33 g. of dissolved solid, containing 23.8 g (0.12 mol) of 2,2,7,7-tetramethyloct-4-ene-3,6-dione and 2.2 g of 2,5-di-tertbutylfuran as shown by gas-liquid chromatographic analysis:

Note 1. The strength of sodium hypochlorite solution decreases on storage and should be checked every few days.
Note 2. A mild exotherm was observed.
Note 3. The quantity of 2 N-hydrochloric acid necessary to bring the pH of the aqueous phase to 8.5 may vary from one preparation to another.
Note 4. By using twice the volume of methylene chloride it is possible to make the organic layer the lower one without adversely affecting the reaction.

I claim:

1. A process for the preparation of 1,4-dialkylbut-2-ene-1,4-diones which comprises oxidising a 2,5-dialkylfuran with an aqueous solution of a sodium, potassium or calcium hypochlorite at a pH from 7 to 10.

2. A process as claimed in claim 1 wherein the pH is from 7.5 to 8.5.

3. A process as claimed in claim 1 wherein the inorganic hypochlorite is sodium hypochlorite.

4. A process as claimed in claim 1 wherein the process is carried out in the presence of an inert organic solvent for the dialkylfuran.

5. A process as claimed in claim 1 wherein the pH of the aqueous phase is initially adjusted to within the desired range by addition of a hydrochloric acid, and thereafter maintained within the desired range by addition of sodium hydroxide.

6. A process as claimed in claim 1 wherein the pH of the aqueous phase is maintained within the desired range by buffering the aqueous hypochlorite solution.

7. A process as claimed in claim 6 wherein the buffer is borax.

* * * * *